(12) United States Patent
Duerr-Myers et al.

(10) Patent No.: US 7,291,593 B2
(45) Date of Patent: Nov. 6, 2007

(54) USE OF FISH FOR TREATING INFERTILITY

(75) Inventors: Louise Duerr-Myers, Lausanne (CH); Ernest Loumaye, Massongy (FR)

(73) Assignee: Laboratoires Serono SA, Coinsins, Vaud (CH)

( * ) Notice: Subject to any disclaimer, the term of this patent is extended or adjusted under 35 U.S.C. 154(b) by 612 days.

(21) Appl. No.: 10/182,138

(22) PCT Filed: Jan. 9, 2001

(86) PCT No.: PCT/GB01/00065

§ 371 (c)(1),
(2), (4) Date: Dec. 17, 2002

(87) PCT Pub. No.: WO01/54715

PCT Pub. Date: Aug. 2, 2001

(65) Prior Publication Data

US 2003/0158106 A1    Aug. 21, 2003

(30) Foreign Application Priority Data

Jan. 27, 2000  (EP) ................................. 00300591
Apr. 4, 2000   (EP) ................................. 00302840

(51) Int. Cl.
*A61K 38/24* (2006.01)
(52) U.S. Cl. .......................................... 514/12; 514/8
(58) Field of Classification Search ...................... None
See application file for complete search history.

(56) References Cited

U.S. PATENT DOCUMENTS 4,725,579 A    2/1988 Jones, Jr. et al.

OTHER PUBLICATIONS

Loumaye et al. Recombinant follicle stimulating hormone: development of the first biotechnology product for the treatment of infertility. Human Reproduction Update 1998, vol. 4, No. 6, pp. 862-881.*
Mickle JE et al. Genotype-phenotype relationships in cystic fibrosis. Med Clin North Am. May 2000;84(3):597-607.*
Voet et al. Biochemistry. 1990. John Wiley & Sons, Inc. 126-128 and 228-234.*
Yan et al. Two-amino acid molecular switch in an epithelial morphogen that regulates binding to two distinct receptors. Science 290: 523-527, 2000.*
Olivennes et al. A protocol using a low dose of gonadotrophin-releasing hormone agonist might be the best protocol for patients with high follicle-stimulating hormone concentrations on day 3. Hum Reprod. Jun. 1996;11(6):1169-72.*
Lashen, Hany et al. "Superovulation with a High Gonadotropin Dose for in Vitro Fertilization: is it Effective?" *Journal of Assisted Reproduction and Genetics*. vol. 15, No. 7, Aug. 1998, pp. 438-443, XP000971180.
Buvat, J. et al. "Purified Follicle-Stimulating Hormone in Polycystic Ovary Syndrome: Slow Administration is Safer and More Effective," *Fertility and Sterility, US, Elsevier Science Inc.*, New York, NY, vol. 52, No. 4, Oct. 1989, pp. 553-559, XP000891970.
Mannaerts, B. et al. "Double-Blind, Randomized, Dose-Finding Study to Assess the Efficacy of the Gonadotrophin-Releasing Hormone Surges in Women Undergoing Ovarian Stimulation with Recombinant Follicle Stimulating Hormone (Puregon)," *Human Reproduction*, IRL Press, Oxford, GB, pp. 3023-3031, XP000876538.
Bennink et al., Ovariële stimulatie; toekomstige behandelingsmogelijkheden, *TFO Tijdschr. Fertiliteitsonderz*, 46054 (1995).
Lolis et al., The follicle-stimulating hormone threshold level for follicle maturation in superovulated cycles, *Fertility and Sterility*, 63(6)1272-1277 (1995).
Lapolt et al., Enhanced stimulation of follicle maturation and ovulatory potential by long acting follicle-stimulating hormone agonists with extended carboxyl-terminal peptides, *Endocrinology*, 131(6)2514-2520 (1992).
P076. Reddy et al., An alternate day step-down regimen using Gonal-F® (rh-FSH) in IVF: a UK multicentre study, *Abstracts of the 12th Annual Meeting of the EHSRE, Mastrict*, p. 130-131 (1996).
Sharma et al., A comparison of treatments with exogenous FSH to promote folliculogenesis in patients with quiescent ovaries due to the continued administration of an LH-RH agonist, *Human Reproduction*, 2(7)553-556 (1987).
Fares et al., Design of a long-acting follitropin agonist by fusing the C-terminal sequence of the chorionic gonadotropin β subunit to the follitropin β subunit, *Proc. Natl. Acad. Sci. USA*, 89:4304-4308 (1992).

* cited by examiner

*Primary Examiner*—Elizabeth C. Kemmerer
*Assistant Examiner*—Gregory S. Emch
(74) *Attorney, Agent, or Firm*—Browdy & Neimark, PLLC

(57) ABSTRACT

The present invention relates to the use of FSH and/or a biologically-active analogue thereof in the production of a medicament for the treatment of infertility in women. The medicament is for administration at an initial dose in the range of from 100 to 600 IU followed by a second dose at least 3 days later in the stimulation phase. In one embodiment, the medicament is for administration of a dose in the range of from 300 to 600 IU on every third day of the first 6 days of the stimulation phase. In another embodiment, the initial dose is in the range of from 100 to 500 IU, with the second dose being administered between three and six, preferably four, days after the initial dose.

19 Claims, No Drawings

USE OF FISH FOR TREATING INFERTILITY

The present invention relates to the use of gonadotrophins in the treatment of subfertile and infertile women.

Ovulatory disturbances are present in approximately 15-25% of couples presenting for an infertility evaluation (Hull, *Gynecol. Endocrinol.* 1:235-245 (1987); Speroff et al., *Clinical Gynecologic Endocrinology and Infertility*, 5$^{th}$ Edition, Baltimore, Williams and Wilkins (1994)). Most infertile anovulatory patients fall into the WHO group II (WHO Scientific Group Report (B Lunenfeld, Chairman), *WHO Techn. Rep. Ser.* 514:1-28 (1973)) category and the great majority of these women are diagnosed as having polycystic ovary syndrome (PCOS) (Hill et al., *In Gynecologic Endocrinology and Infertility*, A C Wenta, C M Herbert III, G A Hill (eds.) Baltimore, Williams and Wilkins, pp147-160 (1988); Speroff et al., *Clinical Gynecologic Endocrinology and Infertility*, 5$^{th}$ Edition, Baltimore, Williams and Wilkins (1994)). In these patients, an anti-oestrogen such as clomiphene citrate is the first line of treatment for ovulation induction, but in those women with PCOS who do not ovulate (around 20% are clomiphene resistant) or do not conceive in response to repeated courses of clomiphene citrate, the alternative method of treatment is usually gonadotropin therapy (Franks and Gilling-Smith, *Curr. Opin. Obstet. Gynecol.* 6:136-140 (1996); The ESHRE Capri Workshop, *Hum. Reprod.* 11:1775-1807 (1996)). Although urinary gonadotropins have proved to be useful for ovulation induction in PCOS patients (Balasch et al., *J. Assist Reprod. Genet.* 13:551-556 (1996)); Hamilton-Fairley et al., *Hum. Reprod.* 6:1095-1099 (1991); White et al., *J. Clin. Endocrinol Metab.* 81:3821-3824 (1996)), today, r-FSH has become a further useful tool to induce ovulation such women in view of its higher efficacy (Balasch et al., (1998) (supra); Coelingh-Bennink et al., *Fertil. Steril.* 69:19-25 (1998)).

The most important principle in ovulation induction is to provide as close as possible a physiological restoration of cyclical ovarian function; in particular, the aim should be to achieve the ovulation of a single follicle. Multiple follicular development is a complication which is characteristic of ovulation induction with exogenous gonadotropins, particular in women having PCOS who are very sensitive to gonadotropin stimulation (Franks and Gilling-Smith, (1996) (supra)). In fact, around 75% of iatrogenic multifoetal pregnancies are due to ovulation induction while the remaining 25% are the product of assisted reproductive techniques (Levene et al., *Br. J. Obstet. Gynaecol.* 99:607-613 (1992); Hecht, *Assist. Reprod. Rev.* 3:75-87 (1993); Evans et al., *Am. J. Obstet Gynecol.* 172:1750-1755 (1995); Corchia et al., *Am. J. Public Health* 86:851-854 (1996)). Also, PCOS is a major risk factor for ovarian hyperstimulation syndrome (Schenker, *Hum. Reprod.* 8:653-659 (1993)).

Treatment of subfertility and infertility by assisted reproduction technologies (ART) such as IVF and embryo transfer (ET) requires ovarian stimulation to increase the number of female gametes, and the chance of a successful treatment outcome (Healy et al, *Lancet*, 1994, 343 : 1539-1544). Currently, standard regimen of ovarian stimulation include a down-regulation phase in which endogenous Luteinising Hormone (LH) is suppressed by administration of a GnRH (Gonadotrophin Releasing Hormone) agonist followed by a stimulation phase in which multiple follicular development (folliculogensis) is induced by daily administration of exogenous Follicle Stimulating Hormone (FSH). Another alternative is to start the stimulation after spontaneous or induced menstruation and prevent occurrence of an ill-timed LH surge by administration of a GnRE-antagonist. When adequate follicular development is achieved, a single dose of urinary human Chorionic Gonadotrophin (u-hCG) can be administered to mimic the endogenous LH surge and provoke oocyte maturation (Loumaye et al, *Human Reproduction Update*, 1995; 1: 188-199).

With the conventional therapy, a daily dose of FSH is administered until an appropriate ovarian response is obtained. This approach involves a prolonged exposure to high levels of FSH, which can prevent the selection of a dominant mature follicle and result in multiple follicular development of both primary and secondary follicles throughout stimulation (Salat-Baroux et al Submitted 1998 to Human Reproduction).

As therapies have developed over the last few years, the initial starting dose of FSH for IVF treatment has decreased (e.g. initially 225 IU was administered -for the first 5 days followed by dose adaptation, then later 150 IU was administered for the first 6 days followed by dose adaptation).

Chronic, low-dose gonadotropins have been widely used over the last decade in a step-up regimen where the starting dose of FSH is 75 IU daily which is gradually (half-ampoule per day) increased as 1- to 2-week intervals in an attempt slowly and prudently to surpass the individual FSH threshold for follicular recruitment (Balasch et al., *J. Assist Reprod. Genet.* 13:551-556 (1996)); Hamilton-Fairley et al., (1991) (supra); White et al., (1996) (sipra); Buvat et al., *Fertil. Steril.* 52:553-559 (1989); Sagle et al., *Fertil. Steril.* 55:56-60 (1991); Shoham et al., *Fertil. Steril.* 55:1051-1056 (1991); Homburg et al., *Fertil. Steril.* 63:729-733 (1995)). Low dose step-up gonadotropin therapy, however, may still lead to overstimulated cycles with multiple follicular development in PCOS patients (Herman et al., *Hum. Reprod.* 8:30-34 (1993)). Thus, the largest series published so far by an outstanding medical team (Hamilton-Fairley et al., (1991) (supra); White et al., (1996) (supra)) and based on 934 treatment cycles indicates that 20% of them were abandoned before completion, in most cases because more than three large follicles developed. There were 72% ovulatory cycles of which 77% were uniovulatory. Overall, these data indicate that ovulation of a single dominant follicle is attained in only around 50% of started gonadotropin treatment cycles (Hamilton-Fairley et al., (1991) (supra); White et al., (1996) (supra)).

On the other hand, a low dose step-down schedule in which a large dose of gonadotropin (150 to 225 IU) is given for an initial 2 or 3 days in order to mirmic physiological secretion of endogenous FSH release, has been reported (Mizunuma et al., *Fertil. Steril.* 55:1195-1196 (1991); van Santbrink et al., *Hum. Reprod.* 10: 1048-1053 (1995)). This is followed either by an approach similar to the step-up protocol (Mizunuma et al., (1991) (supra)) or by a progressive decrease (every 3 days) of daily FSH dose to a minimum of 75 IU/day in order to obtain a subthreshold dose designed to maintain only the growth of the lead follicle (van Santbrink et al., (1995) (supra)). The first option is associated with a low rate (35%) of single dominant follicular development (Mizunuma et al., (1991) (supra)) while the latter led to monofollicular growth in 62% of 234 treatment cycles (van Santbrink et al., (1995) (supra)) but it demands more intense monitoring (Franks & Hamilton-Fairley, Ovulation induction: Gonadotropins. In Adashi E Y, Rock J A, Rosenwaks Z (eds.), Reproductive Endocrinology, Surgery, and Technology, Lippincott-Raven, Philadelphia, pp1207-1223 (1996)) and its reproducibly may be difficult to achieve mainly because of the long half-life of FSH preparations (Baird, Use of gonadotropins to induce ovulation in polycystic ovary syndrome. In Filicori M and Flamigni C (eds.) The Ovary: Regulation, Dysfunction and Treatment. Elsevier Science B.V., Amsterdam, pp391-401 (1996)).

Other FSH administration regimen have been tried. Sharma et al (*Hum Reprod.*, 1987; 2:553-556) compared the response of 150 IU FSH daily and on alternate days, versus 300 IU FSH on alternate days in GnRH pre-treated patients. However, this study was performed in relatively few patients and therefore the results cannot be evaluated as conclusive. Furthermore, it was conducted in 1987 when only urinary-derived FSH preparations were available.

More recently, Reddy et al. (1996, *Abstracts of the 12th Annual Meeting of the EHSRE*) examined the safety and efficiency of a "user-friendly" alternate day step-down regimen in a UK multicentre study. Stimulation with SC Gonal-F® (recombinant human FSH) commenced at a starting dose of 450 IU/day on days 1 and 3, with a step-down on day 5 to 300 IU/day. The 300 IU alternate day regimen continued until hCG criteria were met. The mean duration of the Gonal-F® treatment was 10 days and median dose 1800 IU (equivalent to 24 ampoules of 75 IU) and 83.7% of patients reached hCG administration by day 12. The treatment resulted in a mean of 8.6 follicles of $\geq 14$ mm in diameter on hCG day of administration. It was concluded that a simplified alternate step down regimen can be recommended combining high patient acceptability and the reduced consumption of gonadotrophins with a pregnancy rate comparable to that of conventional regimens. This study did not however include a comparative group receiving conventional IVF therapy to provide a reference for the evaluation of data.

Lolis et al (*Fertil.Steril.*, 1995:63; 1273-1277) have shown that a single IM injection of a high-dose FSH bolus in the early follicular phase of normal women induced a 3-day increase in serum FSH concentrations and this was adequate to stimulate multiple follicular development. However, apart from the dominant one, these follicles were unable to maintain oestrogen production and advance beyond a certain size in the presence of physiological concentrations of FSH. When a stronger FSH stimulus was applied through an increase in serum FSH concentrations during the mid-follicular and late follicular phases by administering extra doses of FSH, a steady rise in serum estradiol ($E_2$) values and a proportional increase in the number of preovulatory follicles were seen.

Although these studies have proposed the use of higher doses of FSH administered at longer time intervals, it has been suggested that exceeding a daily dose of 300 IU is unrewarding (Lashen et al, *J. Assist. Reprod and Genet.* 1998, 15(7): 438-443).

There is a need for improvement of ovulation stimulation protocols.

According to a first aspect of the invention, there is provided the use of FSH and/or a biologically-active analogue thereof in the production of a medicament for the treatment of infertility in women, the medicament being for administration at an initial dose in the range of from 100 to 600 IU followed by a second dose at least 3 days later in the stimulation phase.

For convenience, reference hereinafter to FSH is intended to include biologically-active analogues thereof.

As used herein, the "stimulation phase" is intended to define the point in an assisted reproduction cycle (normally for helping a subfertile or infertile woman to conceive) at which a physician considers that folliculogenesis is to be induced. This may be after endogenous LH has been sufficiently suppressed (normally by administration of a GnRH agonist) e.g. when the level of estradiol is 200 pmol and/or no follicular growth can be visualised using ultrasound and/or the endometrium is thin. Alternatively, this may be following spontaneous or induced menstruation, with the administration of an GnRH-antagonist to prevent an ill-timed LH surge.

In the present invention, "infertile" women include women who cannot ovulate, including those with polycystic ovary syndrome (PCOS), as well as those with normal ovulation who cannot conceive.

Administration of FSH in accordance with the present invention can promote monofollicular development and reduce multifollicular development, decreasing the chances of multiple pregnancies. In addition, such administration may result in a higher pregnancy rate. However, fewer injections are needed which is a significant advantage for the patient. The injections may be self-administered and so the fewer injections required decreases the chances of treatment having to be aborted owing to missed injections. Even when the injections are not self-administered, the present invention provides the advantage that fewer trips are required, whether these be by the patient to a clinic or by a doctor or nurse to the patient.

In one embodiment, FSH is for administration at a dose in the range of from 300 to 600 IU on every third day of the first 6 days of the stimulation phase. The dose is preferably 400-500 IU, more preferably 430 to 470, and most preferably about 450 IU. This embodiment can provide results which are at least the same in terms of follicular development as the conventional administration of 150 IU/day, and can indeed result in a higher pregnancy rate. However, as discussed above, fewer injections are needed (2 as compared to 6 for the conventional regime). In accordance with this embodiment of the invention, FSH is administered every third day of the stimulation phase. It is preferred if administration is on days 1 and 4, although it is possible for FSH to be administered on days 2 and 5 or 3 and 6.

After the first 6 days of the stimulation phase, FSH may be administered at a level to be determined by the physician for adequate follicular development to be achieved. For example, FSH may be administered at a daily dose of 150 IU if ovarian response is adequate, or a dose of 225 IU if it is not adequate. If necessary, these doses may be increased incrementally by 75 IU FSH/day for example.

In another embodiment, the initial dose is in the range of from 100 to 500 IU, with the second dose preferably being administered between three and six, and preferably four, days later. The initial dose is preferably 200-400 IU, more preferably 250-350, and most preferably about 300 IU.

In this embodiment, the second dose may be in the range of from 50 to 200 IU, preferably 70 to 100 IU and most preferably about 75 IU. This embodiment is particularly effective at promoting monofollicular development and reducing multifollicular development. The second dose is preferably repeated daily for 1 to 4 days, preferably 2 days, following which FSH may be administered at a level to be determined by the physician for adequate follicular development to be achieved. For example, FSH may be administered at a daily dose of 75 IU if ovarian response is adequate. If necessary, this dose may be increased incrementally by 37.5 IU FSH/day for example.

In this embodiment of the invention, it is preferred if the initial dose is administered on day 3, although it is possible for it to be administered on days 1, 2 or 4.

After adequate follicular development, a single dose of u-hCG or r-hCG or r-hLH may be administered to provoke oocyte maturation. This may for example be when the largest follicle has reached a mean diameter of at least 18 mm; there are at least two other follicles with a mean diameter $\geq 16$ mm; and the $E_2$ level is within an acceptable range for the number of follicles present.

The present invention can be used in the stimulation of multiple follicular development, preferably prior to in vitro fertilisation (IVF) or Intra-Cytoplasmic Sperm Injection (ICSI), although it may be prior to natural fertilisation.

LH, FSH and hCG may be obtained from natural sources, e.g. isolated from urine, pituitary or placenta, or may be obtained using recombinant DNA technology (see WO85/01959 and Loumaye et al, *Human Reprod.*, 11: 95-107, 1996). Biologically-active analogues thereof include muteins, peptidic analogues, non-peptidic analogues and chimeras. Examples of suitable FSH chimeras are described in WO-A-90/09800, WO-A-93/06844, WO-A-91/16922 and WO-A-92/22568. It is preferred if human FSH is used in the present invention.

The medicament may be packaged so as to provide only the required dose of FSH, e.g. in a unit-dose container such as a vial. However, it is possible that FSH may be administered on two or more occasions during the day—provided of course that total FSH administered during the day equals the required dose—and the medicament packaged accordingly, i.e. in a multi-dose container. Such decisions will be taken by the physician administering the medicament and will depend on parameters such as the patient's body mass index (BMI), medical history, response to the treatment, the half-life of the medicament and so on.

Compounds useful in the invention may be formulated for administration by any convenient route, often in association with a pharmaceutically and/or veterinarily acceptable carrier. It is preferred that the compounds are formulated for parenteral administration.

It is preferred that the FSH be administered subcutaneously, preferably into the anterior abdominal wall.

Formulations for parenteral administration will usually be sterile. Pharmaceutical formulations adapted for parenteral administration include aqueous and non-aqueous sterile injection solutions which may contain anti-oxidantsi buffers, bacteriostats and solutes which render the formulation isotonic with the blood of the intended recipient; aqueous and non-aqueous sterile suspensions which may include suspending agents and thickening agents are also within the scope of the invention. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets. The formulations can be administered through a prefilled syringe, an auto-injector or a multidose auto-injector.

Oral and other enteral formulations need not be sterile and may be presented in unit- or multi-dose form. Oral formulations may be in the form of solids, such as powders, granules, tablets, capsules (for example hard or soft gelatin capsules) or lozenges, or liquids, such as syrups or elixirs. Fillers and/or carriers may be present as appropriate, and those skilled in the art of pharmaceutical formulation will be able to provide such additional or alternative excipients as may be necessary or desirable; flavouring agents are one example. Any formulation intended for oral administration may be formulated for enteric resistance, so as to assist delivery to the small intestine by avoiding or mitigating any digestion of the compound(s) as may occur in the stomach or the proximal part of the small intestine. Tablets or capsules may be enteric coated, for example by conventional procedures. Liquid formulations may be effectively rendered enteric resistant by including or being co-administered with a suitable agent such as medium-chain triglycerides.

Enteral compositions other than oral compositions include rectal compositions, which may be in the form of a suppository. Suppositories will generally include a suppository base, such as cocoa butter. Again, particular formulations containing the active ingredient(s) may routinely be prepared by those skilled in the art of pharmaceutical formulation.

According to a second aspect of the invention, there is provided a method for inducing folliculogenesis in a subfertile or infertile woman, comprising administering FSH and/or a biologically-active analogue at an initial dose in the range of from 100 to 600 IU followed by a second dose at least 3 days later in the stimulation phase.

Preferred features of each aspect of the invention are as for each other aspect, mutatis mutandis.

All patent and literature documents referenced throughout this specification are hereby incorporated by reference to the fullest extent allowed by law.

The invention will now be described further in the following non-limiting examples.

EXAMPLE 1

The following study was designed to (a) assess multiple follicular development after the administration of r-hFSH in intervals of 3 days for the first 6 days of stimulation, followed by daily administration from day 7 onwards, compared to daily administration from day 1 of stimulation, using efficiency endpoints such as the total number of injections during the stimulation phase, the cumulative r-hFSH dose and the duration of r-hFSH treatment, and (b) demonstrate that the alternative dose regimen will result in at least an equivalent clinical efficacy, evaluated by efficacy endpoints such as the number of follicles $\geq 11$ mm and $\geq 14$ mm on day 7 and day of hCG administration and the number of oocytes retrieved.

In summary, patients admitted to the study were infertile women desiring pregnancy, having failed to conceive after at least one year of unprotected coitus and justifying ART (IVF, ICSI), provided that they conformed to certain eligibility criteria which are described in more detail below.

Pituitary down-regulation was achieved by GnRH agonist administration prior to r-hFSH treatment. The r-hFSH dose schedule from day 1 to day 6 of the stimulation phase was as described above. It should be noted that a fixed total dose of 900 IU FSH for all patients was administered from day 1 to day 6 inclusive. Dose titration was allowed based on individual ovarian response (maximum daily dose 450 IU) from day 7. From day. 7 onwards, FSH was administered daily at a dose adjusted to the individual ovarian response, until follicular development was judged to be adequate (assessed by ovarian ultrasound and serum estradiol ($E_2$) concentration). In order to achieve final follicular maturation before ovum pick up (OPU), urinary. human Chorionic Gonadotrophin (u-hCG) was administered in a single dose of 5000 IU. Efficacy included monitoring of the endocrine response to r-hFSH through blood sampling for analysis of $E_2$, FSH, LH and $P_4$ serum levels as well as regular ultrasound examination of the ovaries during the stimulation phase. Efficiency endpoints include the total number of injections, total cumulative dose and duration of treatment. Efficacy endpoints include number of follicles $\geq 11$ mm and $\geq 14$ mm on day 7 and day of hCG administration and number of oocytes retrieved.

Patient Selection 68 patients were selected who met all of the following inclusion criteria:
- An infertile patient defined as: a woman desiring a pregnancy and having failed to conceive after at least one year of unprotected coitus. This infertility must be attributable to at least one of the following and justify an IVF-ET treatment:
- Tubal factor. Inclusion criteria
- Mild endometriosis (American Fertility Society classification stage I or II).
- Male infertility (see conditions below).
- Unexplained
- A male partner with semen analysis within the past six months with $\geq 1.0 \times 10^6$ motile spermatozoa (motility grade A and B) per ml in the ejaculate and an oocyte fertilisation rate $\geq 20\%$ during any previous IVF attempt. If these criteria are met, regular insemination or intracytoplasmic sperm injection (ICSI) may be used. If these criteria are not met, the patient can be entered, but only if ICSI is used.
- Aged 18-38 years.
- Pregnancy excluded prior to beginning oral contraception and/or GnRH agonist therapy.
- A spontaneous ovulatory menstrual cycle of 25-35 days.
- Early follicular phase (Day 2-4) serum levels assayed by local lab. within the ranges defined below:
  - FSH less than 10 IU/l.
  - LH less than 13.5 IU/l.
  - PRL less than 800 IU/l
- Presence of both ovaries.
- No more than three previous assisted reproductive technology (ART) cycles or no more than three previous ART cycles since the last clinical pregnancy.
- Have had at least a wash-out cycle, after the last ART, and/or clomiphene citrate or gonadotrophin treatment, prior to the first day of stimulation (S1)

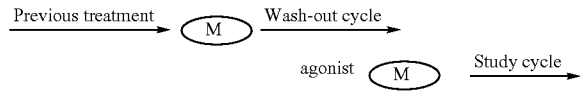

- No previous assisted reproductive technology (ART) cycles indicating a poor response to gonadotrophin stimulation (defined as: maturation of $\leq 2$ follicles)
- No previous history of moderate or severe ovarian hyperstimulation syndrome (OHSS).
- Uterine cavity without abnormalities which could impair embryo implantation or pregnancy evolution as assessed with ultrasound (US), or hysteroscopy (HSC), or hysterosalpingography (HSG) performed within 5 years prior to the first day of the stimulation cycle.
- No known allergy or hypersensitivity to human gonadotrophins preparations.
- A normal cervical PAP smear (to be performed if no smear test was performed during the previous 12 months).

and who did not meet any of the following exclusion criteria:
- Any contraindication to being pregnant and carrying a pregnancy to term.
- Extrauterine pregnancy in the past 3 months.
- Clinically significant systemic disease.
- A body mass index greater than 30 (calculated as body weight (kg) divided by height$^2$(m$^2$)).
- Any medical conditions which may interfere with the absorption, distribution, metabolism or excretion of FSH.
- Abnormal gynaecological bleeding.
- A history of drug, medication or alcohol abuse within the past 5 years.

A maximum of six months before starting down regulation (GnRHa therapy), the following were evaluated:
- Demographic data: Date of birth, height, weight, and race.
- Medical, current medication history and physical examination: Including blood pressure, heart rate, and general health information. Current smoking habits were noted.
- Gynaecological and obstetrical history: Review of previous significant gynaecological and obstetrical history, including data from all previous ART cycles.
- Gynaecological examination: Gynaecological examination (including cervical PAP smear if none has been performed within the past 3 years).

Diagnostic ultrasonography: A pelvic US examination was performed during the early follicular phase using an endovaginal probe. Description of both ovaries included, length in three planes, the number of follicles ≦10 mm present on the largest section through the ovary, the size of any follicles ≧11 mm and the size of any ovarian cysts. The size of the uterus (length, height and width) and its appearance was recorded.

Laboratory screening: Two ml serum was collected and sent to the local lab to determine early follicular phase (day 2-4 of a spontaneous cycle) concentrations of FSH, PRL and LH.

Semen analysis: A semen analysis of the male partner was performed.

The patients were randomised according to a computer-generated randomisation list into two groups. 33 of the patients were allocated to group 1 (150 IU per day) and 35 were allocated to group 2 (450 IU every $3^{rd}$ day).

Medication, Administration and Monitoring

Leuprorelin acetate (Uno-Enantone®, Takeda) was used as the agonist for pituitary gonadotrope cells desensitisation. It was administered at a dose of 0.1 ml containing 0.5 mg per day SC into the thigh once daily, beginning at mid-luteal phase of the menstrual cycle and ending on the day of u-hCG injection. Pituitary desensitisation was confirmed by an ultrasound scan and by measurement of the $E_2$ level at the earliest 10 days after commencement of the treatment. If the patient was not down-regulated at that time, Leuprorelin treatment alone was continued for a further 15 days. In any case, down-regulation was confirmed before beginning the superovulation treatment.

After down-regulation was confirmed, treatment with r-hFSH (Gonal-F®, Serono) was commenced. Gonal-F® was administered either once daily, or every 3rd day, as appropriate, as a SC administration in the abdomen. The starting fixed dose (at day S1) was 150 IU/day or 450 IU FSH/$3^{rd}$ day for 6 days (inclusive). On S7 (7 days after commencement of r-hFSH treatment), the doses were adapted according to the ovarian response monitored by US and serum $E_2$ levels. In this regard, on S1, S5, S7, and each time the patient was seen at the centre for monitoring, including the day of u-hCG administration, a blood sample was collected, centrifuged and the serum (2 ml) used for immediate assessment in the local laboratory for analysis of $E_2$, $P_4$, LH and FSH. Ultrasound examinations were performed with an endovaginal probe on the same days as $E_2$ measurements. On each occasion all follicles with a mean diameter ≧11 mm were measured.

Gonal-F® was supplied in ampoules containing 150 IU of FSH, 30 mg sucrose and phosphate buffer in a lyophilised form. The number of ampoules required for the daily dosage was reconstituted with water for injection and injected SC immediately thereafter. The following Table 1 indicates the specific dilution required when preparing the dose for administration:

TABLE 1

| DOSE (IU) | Number of 150 IU FSH ampoules | Diluent number of ml | Volume of injection (ml) |
|---|---|---|---|
| 150 | 1 | 1 | 1 |
| 225 | 2 | 1.33 | 1 |
| 300 | 2 | 1 | 1 |
| 375 | 3 | 1.2 | 1 |
| 450 | 3 | 1 | 1 |

The dose of FSH was adjusted on day 7 of treatment according to the ovarian response. In both groups, if the ovarian response was sufficient, the dose of 150 IU was used. In both groups, if the ovarian response was not adequate, a dose of 225 IU was used. Subsequently, if the dose was increased, the increment was only 75 IU FSH/day above the previous dose. Thus, daily dosages were only: 150, 225, 300, 375 and 450 IU FSH/day.

A single SC injection of 5000 IU of u-hCG (Profasi®, Serono) was injected the day after the last r-hFSH and GnRH agonist administration, when: the largest follicle had reached a mean diameter of at least 18 mm; at least two other follicles with a mean diameter ≦16 mm were present; and the $E_2$ level was within an acceptable range for the number of follicles present. Profasi® was supplied in ampoules containing 5000 IU u-hCG and 10 mg lactose in freeze-dried, powder form for SC administration. One ampoule of u-hCG was reconstituted with 1.0 ml of saline solution for injection (0.9% NaCl) and a volume of 1.0 ml was injected SC immediately thereafter.

Thirty four to thirty eight hours after u-hCG administration, oocytes were recovered either abdominally or vaginally under ultrasound monitoring. Oocytes were then fertilised in vitro and embryos replaced 2-3 days after oocyte recovery. No more than three embryos were replaced. The following information was recorded:

Number of oocytes: The total number of retrieved oocytes, including fractured and immature ones, was recorded.

Oocyte nuclear maturity: Oocyte nuclear maturity was be assessed every time it was possible. Oocytes were classified as germinal vesicle (the germinal vesicle, or nucleus, of the human oocyte is more or less spherical in shape and usually contains a single, exocentrically placed nucleolus. The germinal vesicle itself is centrally located within the ooplasm in early immature oocytes and becomes more exocentrically located just prior to germinal vesicle breakdown), metaphase I (the metaphase I oocyte is characterised by its lack of association with either a first polar body or a germinal vesicle. Under the light microscope, the typical metaphase I (intermediate) oocyte displays (a) no first polar body and no germinal vesicle; (b) ooplasm that is round and even, usually lightly coloured but sometimes slightly granular), or metaphase II (the typical metaphase II (mature; preovulatory) oocyte displays (a) an extruded first polar body, (b) ooplasm which is round and even, lightly coloured, and homogeneous in granularity).

Degenerative or Atretic Oocytes (nonviable): The presence of degenerative or atretic oocytes was recorded. Degenerative oocytes may exhibit any of the nuclear states described above. Degeneration and atresia may occur in an oocyte at any point along the maturational process within a follicle, from early immature stages to postmature stages. Degeneration produces multiple abnormal morphologic aspects within aspirated oocytes ranging from darkened and vacuolated ooplasm to fragility of supportive structures, especially the zona pellucida. Perhaps the degenerative or atretic oocyte is the simplest to identify because of its strikingly abnormal aspects. Under the light microscope, the degenerative or atretic oocyte may display (a) any form of nuclear condition (polar body, germinal vesicle, neither polar body nor germinal vesicle, or impossible to identify), (b) ooplasm that is brown to black in colour and very irregular in shape.

Number of inseminated oocytes: The number of inseminated oocytes was recorded.

Sperm Characteristics and Insemination: The type of insemination (regular or ICSI) was recorded. For regular insemination, the density of motile spermatozoa in the fertilisation dish was recorded. In the case of Intra-Cytoplasmic Sperm Injection (ICSI) insemination, the source of spermatozoa (ejaculate, epididymis or testis) was recorded.

Grade B: These embryos have more uneven or irregular shaped blastomeres, with mild variation in refractility and no more than 10% fragmentation of blastomeres.

Grade C: These embryos show fragmentation of no more than 50% of blastomeres. The remaining blastomeres must be at least in reasonable (Grade B) condition and with refractility associated with cell viability; the zona pellucida must be intact.

Grade D: These embryos show fragmentation of greater than 50% of blastomeres, some of which may be grossly variant in refractility. Any remaining blastomeres should appear viable.

Natural progesterone (Utrogestan®: 3×200 mg/day) was administered by the vaginal route as luteal phase support, starting after the OPU (ovum pick up). Progesterone treatment was continued up to menstruation or, if the patient was pregnant, for at least the first three weeks of pregnancy.

Pregnancy was diagnosed as follows. If the patient did not menstruate, a blood sample was collected approximately fifteen days after u-hCG day of administration for serum hCG assessment. The hCG assessment was repeated on day 23-25 if the serum concentration is ≧10 IU/l. An ultrasound scan was performed between day u-hCG 35 and 42 on all patients who become pregnant, provided that no miscarriage has occurred. The number of foetal sacs and foetal heart activity was recorded.

TABLE 2 summarises the assessments made during the treatment period.

|  | Preg. Test | $E_2$ | Ultrasound | Serum hCG | FSH | $P_4$ | LH |
|---|---|---|---|---|---|---|---|
| GnRH Agonist | X | | | | | | |
| Between day 10 and day 25 of GnRH-a down regulation | | X | X | | X | X | X |
| S1 (Start r-hFSH Treatment) | | X | X | | X | X | X |
| S5 | | X | X | | X | X | X |
| S7 | | X | X | | X | X | X |
| Sn | | X | X | | X | X | X |
| hCG Day | | X | X | | X | X | X |
| Day 15-20 (if no Menstruation) | | | | X | | | |
| Day 23-25 * | | | | (X)* | | | |
| Day 35-42 (pregnant)** | | | (X)** | | | | |

* If first serum hCG is ≧ 10 IU/l
**if pregnant

Fertilisation and Embryo Development: On day 1 after OPU, fertilisation was assessed and the number of mono-, bi- and multi-pronucleate eggs recorded. On day 2 after OPU, the number of cleaved embryos, the number of embryos replaced, the stage of development and morphological score of each embryo at the time of transfer, and the outcome of each embryo (transferred, frozen or discarded) was documented.

The grading system was follows:

Grade A: These embryos show evenly sized blastomeres of near spherical appearance with moderate refractility (i.e. not very dark) and with intact zona. Allowance must be made for the appearance of blastomeres that are in division or that have divided asynchronously with their contemporaries, e.g. 3, 5, 6 or 7 cell embryos. These may be uneven but are perfectly normal.

Serum samples were prepared and stored as follows. In order to obtain 3.5 ml serum, a minimum of 7 ml of venous blood was taken in accordance with standard procedure at the target times given in the table above. Blood samples were allowed to clot for 1 hour at room temperature, spun and serum transferred into 1 aliquot of 2.5 ml (in a 5.0 ml vacutainer), and 1 aliquot of 1 ml. The 2.5 ml aliquot was used for parameter analysis immediately after preparation: the back-up sample of 1 ml was stored frozen at −20° C. Deep freezing of the serum was done as soon as possible after centrifugation but within 4 hours of collection FSH samples were taken as follows. 3 ml of blood will be taken at the target times given in the table above and handled as described above. Serum was transferred into 2 aliquots of at least 500 μl, one of which was retained frozen at −20° C. as a back-up sample. Methods used for the determination of hormones were as follows:

$E_2$: ACS 180 Chiron Chemiluminisent, ELISA.
$P_4$: ACS 180 Chiron Chemiluminisent, ELISA.
FSH: ACS 180 Chiron Chemiluminisent, ELISA
LH: ACS 180 Chiron Chemiluminisent, ELISA.
PRL: ACS 180 Chiron Chemiluminisent, ELISA.

Results

The results of the study are shown in the tables below. Statistical analysis was performed by Serono Corporate Biometrics, using SAS statistical software (SAS Institute, NC, USA).

Both treatment groups had comparable demographic data. The total cumulative dose of FSH required to complete stimulation treatment is also highly comparable. However, the number of injections that the patient had to undergo in order to achieve adequate stimulation is statistically significantly different (p-value: 0.0001). For the comparator treatment group, the mean number of injections is 10.5 (s.d 2.4), whereas for the alternate dose treatment group, the mean number of injections is 6.9 (s.d. 2.2).

The number of oocytes retrieved from both treatment groups is comparable, reflected in the comparable number of oocytes inseminated; Mean number in comparator group is 7.7 (s.d. 5.2) compared to the alternate dose group mean of 6.9 (s.d. 3.1). The number of cryopreserved embryos and viable embryos was statistically significant in favour of the comparator group (p-values 0.0238 and 0.0319 respectively). However, the quality of embryos transferred showed a trend of more Grade A embryos being transferred in the alternate dose group, although this did not reach statistical significance with the amount of patients treated so far.

However, the implantation rate reaches a statistically significant difference in favour of the alternate dose treatment group (p-value: 0.0561) with a mean implantation rate of 18% for this group versus a mean implantation rate of 5% for the comparator treatment.

Furthermore and clinically most relevant (see Table 5—Biochemical and Clinical Pregnancies), the difference in the number of biochemical pregnancies is highly statistically significant (p-value: 0.0038) in favour of the alternate dose treatment group: mean number of biochemical pregnancies 39.4% versus only 8.6% in the comparator treatment group. This resulted in a clinical pregnancy rate which was again statistically significant (p-value: 0.0105) in favour of the alternate dose treatment group: mean clinical pregnancy rate of 30.3% for the alternate dose group versus 5.7% for the comparator treatment group. These data strongly suggest that the serum FSH profile achieved with the new regimen irrespectively result in higher quality, more viable oocytes.

TABLE 3

Summary Statistics

| | Treatment Randomized | | | | | | | | | | | |
|---|---|---|---|---|---|---|---|---|---|---|---|---|
| | 150 IU | | | | | | 450 IU | | | | | |
| Variable | N | Missing | Mean | SD | Min. | Max. | N | Missing | Mean | SD | Min. | Max. | p-value * |
| Age (year) | 35 | 0 | 31.5 | 4.8 | 20 | 39 | 33 | 0 | 31.1 | 3.4 | 23 | 38 | 0.7169 |
| Duration of Infertility (months) | 32 | 3 | 50.0 | 33.2 | 12 | 120 | 32 | 1 | 47.0 | 29.0 | 13 | 125 | 0.7016 |
| No. Previous ART | 35 | 0 | 0.8 | 1.0 | 0 | 3 | 33 | 0 | 0.7 | 0.9 | 0 | 3 | 0.5629 |
| Cumulative FSH Dose (IU) | 35 | 0 | 1748.6 | 630.9 | 900 | 3675 | 33 | 0 | 1743.2 | 538.3 | 1050 | 3675 | 0.9700 |
| No. Injections | 35 | 0 | 10.5 | 2.4 | 6 | 17 | 33 | 0 | 6.9 | 2.2 | 3 | 13 | 0.0001 |
| No. Follicles >= 11 mm | 35 | 0 | 10.9 | 3.7 | 4 | 21 | 33 | 0 | 10.2 | 2.9 | 5 | 16 | 0.3872 |
| No. Follicles >= 14 mm | 35 | 0 | 10.1 | 4.0 | 4 | 21 | 33 | 0 | 9.0 | 2.5 | 5 | 14 | 0.1881 |
| No. Oocytes Retrieved | 35 | 0 | 10.7 | 6.3 | 0 | 26 | 33 | 0 | 8.5 | 3.9 | 3 | 18 | 0.0909 |
| No. Oocytes Inseminated | 35 | 0 | 7.7 | 5.2 | 0 | 19 | 33 | 0 | 6.9 | 3.1 | 3 | 18 | 0.4727 |
| No. 2 PN Oocytes | 35 | 0 | 3.7 | 3.6 | 0 | 14 | 33 | 0 | 3.0 | 1.9 | 0 | 8 | 0.3531 |
| No. Cryopreserved Embryos | 35 | 0 | 1.5 | 2.7 | 0 | 10 | 33 | 0 | 0.4 | 1.0 | 0 | 4 | 0.0238 |
| No. Viable Embryos | 30 | 5 | 3.8 | 3.1 | 1 | 12 | 33 | 0 | 2.6 | 1.1 | 1 | 6 | 0.0319 |
| No. Transferred Embryos | 30 | 5 | 2.0 | 0.6 | 1 | 3 | 33 | 0 | 2.2 | 0.6 | 1 | 3 | 0.3238 |
| No. Embryos Grade A | 30 | 5 | 0.27 | 0.64 | 0 | 2 | 33 | 0 | 0.58 | 0.97 | 0 | 3 | 0.1446 |
| No. Embryos Grade B | 30 | 5 | 1.27 | 1.05 | 0 | 3 | 33 | 0 | 1.18 | 0.98 | 0 | 3 | 0.7414 |
| No. Embryos Grade C | 30 | 5 | 0.47 | 0.73 | 0 | 2 | 33 | 0 | 0.39 | 0.75 | 0 | 3 | 0.6979 |
| No. Embryos Grade D | 30 | 5 | 0.00 | 0.00 | 0 | 0 | 33 | 0 | 0.00 | 0.00 | 0 | 0 | NA |
| Implantation Rate | 30 | 5 | 5.0% | 0.2 | 0.0% | 100% | 33 | 0 | 18.0% | 0.3 | 0.0% | 100% | 0.0561 |

* p-values from ANOVA

TABLE 4

Distribution of the Grading of Embryos Transferred

| | Treatment Randomized | | | |
|---|---|---|---|---|
| | 150 IU | | 450 IU | |
| Grading of Embryos* | N | % | N | % |
| No. Embryos Grade A | 8 | 13.3% | 19 | 26.8% |
| No. Embryos Grade B | 38 | 63.3% | 39 | 54.9% |
| No. Embryos Grade C | 14 | 23.3% | 13 | 18.3% |
| Total | 60 | 100.0% | 71 | 100.0% |

*No embryo of grade D

TABLE 5

Biochemical and Clinical Pregnancies

| Biochemical Pregnancy | Treatment Randomized | | | | |
|---|---|---|---|---|---|
| | 150 IU | | 450 IU | | |
| | N | % | N | % | p-value* |
| Yes | 3 | 8.6% | 13 | 39.4% | 0.0038 |
| No | 32 | 91.4% | 20 | 60.6% | |
| Total | 35 | 100.0% | 33 | 100.0% | |

| Clinical Pregnancy | Treatment Randomized | | | | |
|---|---|---|---|---|---|
| | 150 IU | | 450 IU | | |
| | N | % | N | % | p-value* |
| Yes | 2 | 5.7% | 10 | 30.3% | 0.0105 |
| No | 33 | 94.3% | 23 | 69.7% | |
| Total | 35 | 100.0% | 33 | 100.0% | | p-values from Fisher's exact test

TABLE 6

Summary Statistics

Gonal-F 450 IU every 3rd day for 6 days (inclusive)

| Variable | N | Missing | Mean | SD | Minimum | Maximum |
|---|---|---|---|---|---|---|
| Age (year) | 33 | 0 | 31.1 | 3.4 | 23 | 38 |
| Duration of Infertility (months) | 32 | 1 | 47.0 | 29.0 | 13 | 125 |
| No. Previous ART | 33 | 0 | 0.7 | 0.9 | 0 | 3 |
| Cumulative FSH Dose (IU) | 33 | 0 | 1743.2 | 538.3 | 1050 | 3675 |
| No. Injections | 33 | 0 | 6.9 | 2.2 | 3 | 13 |
| No. Follicles >= 14 mm | 33 | 0 | 9.0 | 2.5 | 5 | 14 |
| Clinical Pregnancy | | | n = 10 (30.3%) | | | |

It will be seen from the results that injection of 450 IU of FSH every $3^{rd}$ day gives at least the same results in terms of follicular development, and may result in a higher pregnancy rate. However, fewer injections are needed.

EXAMPLE 2

The following example compares ovarian performance and hormonal levels after ovarian stimulation in patients with polycystic ovary syndrome (PCOS) using recombinant follicle-stimulating hormone (r-FSH) in two consecutive cycles according to two different low dose gonadotropin regimens, the classic chronic step-up protocol and a modified step-down protocol. The latter protocol is also used in normally ovulating women undergoing their first cycle of intrauterine insemination.

Materials and Methods

In all, 30 primary infertility women were included. Ten of them (Group 1) had PCOS and were studied in 20 treatment cycles. The mean (±SE) age of the patients was 31.8±1.2 years and their mean duration of infertility was 4.1±1.5 years. They presented with oligomenorrhea or amenorrhea, the mean basal LH/FSH radio was 2.8±0.35 and their mean basal androstenedione and free testosterone levels were 305±36 ng/dl (normal values 60-200 ng/dl) and 7.76±3.81% (normal values 0.3-3.8%), respectively. Their mean body mass index was 26.4±1.6, and all them had the ultrasonographic appearance of polycystic ovaries (Adams et al., *Br. Med. J.* 293:355-359 (1986)). Endogenous estrogen activity was evident in these patients by mean basal oestradiol levels of 93.7±10.1 pg/ml and a positive response to a progestin challenge test (normal withdrawal bleeding after treatment with oral medroxyprogesterone acetate, 10 mg daily for 5 days) in each of them. Normal male partner semen parameters, a normal hysterosalpingogram or laparoscopy, and no history of pelvic surgery and/or pelvic inflammatory disease were recorded previously to ovulation induction in these patients. All of them either had failed to ovulate with

TABLE 7

Summary Statistics

| | Treatment Randomized | | | | | | | | | | |
|---|---|---|---|---|---|---|---|---|---|---|---|
| | 150 IU | | | | | 450 IU | | | | | |
| Variable | N | Mean | SD | Min | Max | N | Mean | SD | Min | Max | p-value * |
| Age (year) | 35 | 31.5 | 4.8 | 20 | 39 | 33 | 31.1 | 3.4 | 23 | 38 | 0.7169 |
| Duration of Infertility (months) | 32 | 50.0 | 33.2 | 12 | 120 | 32 | 47.0 | 29.0 | 13 | 125 | 0.7016 |
| No. Previous ART | 35 | 0.8 | 1.0 | 0 | 3 | 33 | 0.7 | 0.9 | 0 | 3 | 0.5629 |
| Cumulative FSH Dose (IU) | 35 | 1748.6 | 630.9 | 900 | 3675 | 33 | 1743.2 | 538.3 | 1050 | 3675 | 0.9700 |
| No. Injections | 35 | 10.5 | 2.4 | 6 | 17 | 33 | 6.9 | 2.2 | 3 | 13 | 0.0001 |
| No. Follicles >= 14 mm | 35 | 10.1 | 4.0 | 4 | 21 | 33 | 9.0 | 2.5 | 5 | 14 | 0.1881 |
| Clinical Pregnancy ** | | n = 2 (5.7%) | | | | | n = 10 (30.3%) | | | | 0.0105 |

* p-values from ANOVA
** p-values from Fisher's exact test clomiphene citrate or had not conceived after at least three ovulatory cycles on this treatment at doses ≦200 mg/day for 5 days.

The PCOS patients were treated with s.c. r-FSH (Gonal-F, Serono S. A., Madrid, Spain) according to a standard low-dose protocol reported previously (Balasch et al., *J. Assist Reprod. Genet.* 13:551-556 (1996)) in their first study treatment cycle and then by a modified step-down regimen in the second gonadotropin treatment cycle. The time interval between treatment cycles in each woman was 1 to 3 months. r-FSH therapy was commenced on day 3 of a spontaneous cycle or of induced uterine bleeding. As ovarian performance and hormonal levels, but not pregnancy rate were the objectives to be compared, 10 consecutive PCOS patients who did not become pregnant in the first treated cycle were included in the present study.

The chronic low dose step-up regimen consisted of administration of a starting dose of 75 IU r-FSH per day and increased, if necessary, by increments of 37.5 IU. The first increase in daily dose was performed after 14 days of therapy only if there was no evidence of an ovarian response on ultrasound (i.e., no follicle >10 mm in diameter). Further dose adjustments were performed if necessary after a period of 7 days. This stepwise increase was continued until ovarian activity was seen on ultrasound; then, the same dose (i.e., the threshold dose) was continued until follicular diameter was >17 mm.

In the modified step-down protocol, patients received 4 ampoules (300 IU) of r-FSH on cycle day 3 and no treatment was given on the next 3 days (cycle days 4 to 6). r-FSH therapy was reinitiated on cycle day 7 by administering 1 ampoule per day of r-FSH after pertinent ultrasound scanning of the ovaries had been performed. This dose was maintained until cycle day 9 (i.e. 1 week since treatment was started) and then the protocol was exactly the same than that in the low dose step-up approach. Thus, each woman was her own control for ovarian performance and hormonal levels studies. The use of the same treatment protocol applied to different gonadotropin drugs in the same patient as previously done by Balasch et al., *Hum. Reprod.* 10:1678-1683 (1995); Balasch, et al., *J. Assist Reprod. Genet.* 15:552-559 (1998); Couzinet et al., *J. Clin. Endocrinol. Metab.* 66:552-556 (1988); Shoham et al., *Fertil. Steril.* 56:1048-1053 (1991) seems the more appropriate study design when ovarian performance and hormonal levels, but not pregnancy rate, are the objectives to be compared.

The modified step-down protocol was also tested in 20 normally ovulatory infertile women (Group 2) having normal ovarian morphology in vaginal ultrasonography. They underwent their first intrauterine insemination cycle in association with ovarian gonadotropin treatment because of unexplained infertility or male subfertility after patent tubes had been diagnosed by hysterosalpingogram or laparoscopy. The mean age of patients in group 2 was 32.9±2.0 years, and their mean duration of infertility was 5.3±1.2 years.

Ovarian response in both groups of patients was monitored by vaginal ultrasound scanning and oestradiol measurements. In addition, for this study, midluteal (7 days post-HCG injection) serum progesterone levels were measured retrospectively in all treatment cycles for patients in group 1. This was done using frozen serum samples stored at −20° C. which were examined in one run. Hormones were measured using commercially available kits according to methods previously reported (Balasch et al., *Hum. Reprod.* 11:2591-2594 (1996)). Oestradiol and progesterone concentrations in serum were estimated by direct radioimmunoassay (bioMérieux, Marcy l'Etoile, France for oestradiol; Immunotech International, Marseille, France for progesterone). For oestradiol, the intraassay and interassay coefficients of variation were <4.5% and <5.5%, respectively, and the former for progesterone was 6.5%.

Serial ultrasound scanning was carried out to determine follicular growth and eventual changes of ovarian diameter. hCG (Profasi; Serono S. A.), 10,000 IU i.m. was given to induce ovulation when the leading follicle reached >17 mm. Ultrasonic scans were performed with a 5 mHz vaginal transducer attached to an Aloka sector scanner (model SSD-620, Aloka, Tokyo).

Data were analysed by SPSS statistical software using the Wilcoxon matched-pairs signed-ranks rest and the chi-square test as appropriate. Results are expressed as means with SE.

Results

All gonadotropin treated cycles included in the present example were ovulatory according to ultrasonographic data, basal body temperature records, the length of the luteal phase, and for patients in group 1, also midluteal serum progesterone concentration >10 ng/ml.

Among PCOS patients (group 1), there was 1 ongoing pregnancy and 1 spontaneous first trimester abortion with the modified step-down approach. Comparative results of the two r-FSH treatment modalities in this group of women are summarised in Tables I and II. The total quantity of FSH used to induce ovulation in PCOS patients was higher with the step-down method despite the fact that both the mean duration of treatment and the threshold dose were similar with the two approaches. However, the rate of multifollicular cycles (i.e., a leading follicle >17 mm and two or more secondary follicles) was significantly higher with the step-up protocol whereas unifollicular cycles (i.e. only one follicle developed that reached >17 mm in diameter) were obtained in as much as 80% of treatment cycles with the step-down method (Table I). Data on follicular dynamics and oestradiol levels during r-FSH treatment in both study groups are presented in Table II. Selective oocyte retrieval was carried out in two multifollicular cycles before HCG injection in this latter treatment group. Four and three oocytes (5 of them immature), respectively, were obtained in these retrievals but no in vitro feitilisation was attempted according to couples preference. Accordingly with final follicular development, oestradiol serum levels on the HCG day were 71% higher with the step-up protocol (difference showing a trend for statistical significance, P=0. 1), whilst midluteal serum progesterone was significantly (P<0.05) higher (Table I).

For patients in group 2 undergoing gonadotropin ovarian stimulation in intrauterine insemination cycles, the days of gonadotropin treatment and the number of ampoules of r-FSH used were 6.1±1.2 and 9.0±1.4, respectively. The daily effective (threshold) dose was 75 IU (1 ampoule) for each treated cycle. As much as 15/20 (75%) treated cycles were unifollicular whilst a secondary follicle accompanying the leading follicle on the HCG day was observed in the remaining 5 cases (25% of bifollicular cycles) but no multifollicular development was obtained. The mean oestradiol serum levels on treatment day 4 and on the day of HCG injection were 89.8±14.7 pg/ml and 271±29.7 pg/ml, respectively. There were three singleton ongoing pregnancies (>14 weeks gestation) among 20 treatment cycles, two of them occurring during unifollicular cycles.

TABLE 1

| Parameter | Step-up | Step-down | P |
|---|---|---|---|
| No. of treatment cycles | 10 | 10 | |
| RFSH required | | | |
| Days of treatment (no.) | 15.7 ± 2.0 | 14.6 ± 2.0 | NS |
| Ampoules (no.) | 16.6 ± 2.8 | 19.1 ± 2.2 | <0.05 |
| IU | 1245 ± 217 | 1436 ± 167 | <0.05 |
| Threshold dose | 87.5 ± 8.8 | 86.2 ± 8 | NS |
| Follicular development on HCG day | | | |
| Unifollicular cycles (%) | 60 | 80 | |
| Bifollicular cycles (%) | 0 | 20[a] | <0.05 |
| Multifollicular cycles (%) | 40 | 0 | |
| Estradiol on HCG day (pg/ml) | 474 ± 90 | 277 ± 38 | NS |
| Midluteal progesterone (pg/ml) | 19.2 ± 2.1 | 16.4 ± 1.9 | <0.05 |

Values are means ± SE
NS = not significant
[a]Two cycles had one secondary follicle measuring 14 and 15 mm in diameter, respectively.

TABLE II

| Parameter | Treatment day | Step-up | Step-down | P |
|---|---|---|---|---|
| Growing follicles (≧11 mm) | 4 | — | 0 | — |
| | 8 | 1.1 ± 0.2 | 0.2 ± 0.1 | <0.05 |
| Oestradiol (pg/ml) | 4 | — | 58.7 ± 8.9 | — |
| | 8 | 106.7 ± 30.2 | 69.1 ± 8.8 | <0.01 |

Values are means ± SE

Discussion

The present example shows a remarkably high incidence (80%) of monofollicular cycles, a 100% incidence of mono or bifollicular cycles, and the absence of multifollicular development. This fact, together with lower serum oestradiol levels on the day of HCG, imply reduced chances for multiple pregnancy and ovarian hyperstimulation.

A randomised study comparing low dose step-up (18 patients) and step-down dose (17 patients) regimens showed 56% and 88% of monofollicular cycles in the first and latter treatment schedules, respectively (van Sanbrink and Fauser, *J. Clin. Endocrinol. Metab.* 82:3597-3602 (1997)). This was a randomised study where patients supposedly having the same endocrine abnormality received one of two treatment approaches at random. However, PCOS is a heterogeneous condition with distinct endocrine features. The FSH threshold varies for individual patients, thus suggesting variable abnormalities (Fauser et al., *Endocr. Rev.* 18:71-106 (1997); Baird, (1996) (supra)). Therefore, as discussed above, the use of the same gonadotropin drug applied to different treatment protocols in the same patient seems the more appropriate study design when ovarian performance and hormonal levels but not pregnancy rate is the objective to be compared. In the present example, each woman was her own control for ovarian activity and hormonal changes. The use of each woman as her own control precludes any carry-over effect from the previous cycle that could affect these results as each PCOS patient had the step-up approach first. In addition, the time interval between treatment cycles in each women was 1 to 3 months.

In the study of van Santbrink and Fauser (van Santbrink and Fauser (1997) (supra)), after a conventional initial dose of gonadotropin was given, a gradual reduction of the dose was employed. However, in the present example a period of coasting was used. Coasting is feasible as the half life of r-FSH is around 36 h (Le Cotonnec et al., (1994) (supra); Le Cotonnec et al., *Fertil. Steril.* 61:669-678 (1994)). It has been suggested that coasting can rescue cycles prone to develop ovarian hyperstimulation, thus indicating that a pronounced decrease in serum FSH concentrations prevents the further development of medium-sized follicles, whereas large follicles continue to mature (van Santbrink et al., (1995) (supra)). However, it is also known that, during coasting, a sudden drop of oestradiol concentration can occur that leads to cycle cancellation (Sher et al., *Hum. Reprod.* 10:3107-3109 (1995); Aboulghar et al., *Hum. Reprod.* 13(Abstract Book 1):243-244 (1998)). This has been observed both in ovulation induction in anovulatory women and during controlled ovarian hyperstimulation. Therefore, in order to avoid cancellation, in the present example a high starting dose was applied to mimic the natural cycle thus promoting follicular recruitment, to be followed later by small stepwise increments if necessary which may be critical in determining follicular maturation (Franks and Hamilton-Fairley, (1996) (supra)).

The great majority of women undergoing intrauterine insemination treatment are ovulatory and it has been stressed that the intensity of ovarian stimulation protocols used for superovulation in intrauterine insemination cycles is related to multiple-pregnancy rate (te Velde and Cohlen *N. Engi. J. Med.* 340:224-226 (1999)). Thus, mild gonadotropin ovarian stimulation regimens which can achieve acceptable success rates but with a low proportion of twins and no higher-order pregnancies (Balasch et al., *Hum. Reprod.* 9:1863-1866 (1994); Cohlen et al., *Hum. Reprod.* 13:1553-1558 (1998)) are being advocated (te Velde and Cohlen, (1999) (supra)). The step-down regimen applied to normally ovulating women in accordance with the present invention represents a new approach in this regard. The 100% rate of monofollicular/bifollicular cycles obtained in Group 2 women adds further evidence favouring the usefulness of this approach when multifollicular development is not desired in ovulation induction.

In summary, a physiological step-down approach for ovulation induction in PCOS patients women may be more appropriate in order to achieve monofollicular cycles than the step-up approach. Also, this modified approach seems to be useful to obtain unifollicular development in normally ovulatory women undergoing ovarian stimulation in intrauterine insemination cycles.

The invention claimed is:

1. A method for treating infertility in women, comprising administering FSH and/or a biologically active analogue thereof to a patient in need thereof at an initial dose in the range of from 100 to 600 IU followed by a second dose at least 3 days later in the stimulation phase.

2. The method of claim 1, wherein the FSH and/or a biologically active analogue thereof is administered at a dose in the range of from 300 to 600 IU on every third day of the first 6 days of the stimulation phase.

3. The method of claim 2, wherein the dose is in the range of from 400 to 500 IU.

4. The method of claim 3, wherein the dose is in the range of from 430 to 470 IU.

5. The method of claim 4, wherein the dose is about 450 IU.

6. The method of any one of claims 2 to 5, wherein the FSH and/or a biologically active analogue thereof is administered on days 1 and 4, days 2 and 5, or days 3 and 6 of the stimulation phase.

7. The method of claim 1, wherein the initial dose is in the range of from 100 to 500 IU.

8. The method of claim 7, wherein the initial dose is in the range of from 200 to 400 IU.

9. The method of claim 8, wherein the initial dose is in the range of from 250 to 350 IU.

10. The method of claim 9, wherein the initial dose is about 300 IU.

11. The method of any one of claims 7 to 10, wherein the second dose is administered between three and six days after the initial dose.

12. The method of claim 11, wherein the second dose is administered four days after the initial dose.

13. The method of any one of claims 7 to 9, wherein the second dose is in the range of from 50 to 200 IU.

14. The method of claim 13, wherein the second dose is in the range of from 70 to 100 IU.

15. The method of claim 14, wherein the second dose is about 75 IU.

16. The method of any one of claims 7 to 10, wherein the second dose is repeated daily for 1 to 4 days.

17. The method of any one of claims 7 to 10, wherein the initial dose is administered on day 1, 2, 3 or 4 of the stimulation phase.

18. The method of claim 1 wherein the FSH is recombinant FSH (r-FSH).

19. The method of claim 1 wherein the FSH is human FSH (hFSH).

* * * * *

UNITED STATES PATENT AND TRADEMARK OFFICE
CERTIFICATE OF CORRECTION

PATENT NO. : 7,291,593 B2  
APPLICATION NO. : 10/182138  
DATED : November 6, 2007  
INVENTOR(S) : Duerr-Myers et al.

Page 1 of 1

It is certified that error appears in the above-identified patent and that said Letters Patent is hereby corrected as shown below:

On the Title Page item (54) and Col. 1, line 1 correct the title from "USE OF FISH FOR TREATING INFERTILITY" to --USE OF FSH FOR TREATING INFERTILITY--;
At column 2, line 58, correct "mirmic" to read --mimic--;
At column 6, line 7, correct "anti-oxdantsi buffers" to read --anti-oxidant, buffers--;
At column 6, line 31, correct "From day. 7 onwards" to read --From day 7 onwards--;
At column 6, line 36, correct "urinary, human Chorionic Ganadotrophin" to read --urinary human Chorionic Ganadotrophin--.

Signed and Sealed this

Thirteenth Day of March, 2012

David J. Kappos  
*Director of the United States Patent and Trademark Office*